(12) United States Patent
Jiang (10) Patent No.: US 7,349,731 B2
(45) Date of Patent: Mar. 25, 2008

(54) RECONSTRUCTED REFRACTIVE INDEX SPATIAL MAPS AND METHOD WITH ALGORITHM

(75) Inventor: Huabei Jiang, Clemson, SC (US)

(73) Assignee: Clemson University Research Foundation, Clemson, SC (US)

(*) Notice: Subject to any disclaimer, the term of this patent is extended or adjusted under 35 U.S.C. 154(b) by 982 days.

(21) Appl. No.: 10/447,872

(22) Filed: May 29, 2003

(65) Prior Publication Data

US 2004/0087861 A1    May 6, 2004

Related U.S. Application Data

(60) Provisional application No. 60/387,208, filed on Jun. 7, 2002.

(51) Int. Cl.
*A61B 6/00* (2006.01)
(52) U.S. Cl. ............ 600/473; 600/342; 600/182
(58) Field of Classification Search ........... 600/310, 600/473; 356/446, 484
See application file for complete search history.

(56) References Cited

U.S. PATENT DOCUMENTS

| | | | | |
|---|---|---|---|---|
| 5,410,413 A | * | 4/1995 | Sela | 356/446 |
| 5,416,582 A | * | 5/1995 | Knutson et al. | 356/484 |
| 5,610,399 A | * | 3/1997 | Muller et al. | 250/341.1 |
| 5,676,142 A | * | 10/1997 | Miwa et al. | 600/310 |
| 6,075,610 A | * | 6/2000 | Ueda et al. | 356/432 |
| 6,178,346 B1 | * | 1/2001 | Amundson et al. | 600/473 |
| 2002/0135752 A1 | * | 9/2002 | Sokolov et al. | 356/39 |
| 2003/0114732 A1 | * | 6/2003 | Webler et al. | 600/121 |

OTHER PUBLICATIONS

Jiang et al., "Simultaneous reconstruction of optical absorption and scattering maps in turbid media from near-infrared frequency-domain data", 1995, Optics Letters, vol. 20, No. 20, pp. 2128-2130.*
Jiang et al., "Optical image reconstruction using frequency-domain data: simulations and experiments", 1996, Optical Society of America, vol. 13, No. 2, pp. 253-266.*
Pierce et al., "Measurement of particle-size distribution and volume fraction in concentrated suspensions with photon migration techniques", 1997, Applied Optics, vol. 36, No. 15, pp. 3310-3318.*
*Phase-Contrast Imaging of Tissue Using Near-Infrared Diffusing Light*, Huabei Jiang and Yong Xu, Med.Phys. 30(6), Jun. 2003, pp. 1048-1051.
*Phase-Contrast Diffuse Optical Tomography*, Huabei Jiang and Yong Xu, Department of Physics and Astronomy, Clemson University, Clemson, SC; Submitted to Nature Magazine, Feb. 28, 2003, pp. 1-11.

* cited by examiner

*Primary Examiner*—Brian L. Casler
*Assistant Examiner*—Nasir Shahrestani
(74) *Attorney, Agent, or Firm*—Kennedy Covington Lobdell & Hickman, LLP (57) ABSTRACT

The invention provides a means to produce reconstructed refractive index spatial maps that reveal and allow visual separation of normal soft tissue and certain types of tumors. Detector fiber optic bundles positioned on the surface of a soft tissue organ receive and transmit scattered light data, from light in the near-infrared portion of the spectrum delivered to the surface of the organ by separate fiber optic bundles to a computer. Based on an established grid and certain assumed values, the data are analyzed by means of a complex algorithm to produce calculated refractive index values. Through iteration, the values are recalculated to minimize the difference between the observed scattering and calculated values to yield a stable map indicating spatial variation in refractive index and such variation in the form of displayed images indicates the presence of tumors in normal soft tissue.

5 Claims, 8 Drawing Sheets

RECONSTRUCTED REFRACTIVE INDEX SPATIAL MAPS AND METHOD WITH ALGORITHM

PRIORITY

This Patent Application claims priority of U.S. provisional Patent Application 60/387,208 filed Jun. 7, 2002 by Jiang and entitled "Algorithm to Generate Refractive Index Spatial Map to Detect Tumors."

The U.S. Government has a paid-up license in this invention and the right in limited circumstances to require the patent owner to license others on reasonable terms as provided for by the terms of R01 Ca 905334, national Institutes of Health, through the national Cancer Institute.

FIELD OF THE INVENTION

The utility of the invention is found in the clinical field of tumor detection, specifically in the area of non-invasive means to detect tumors in soft tissue and to distinguish benign from malignant tumors. The technology is found in optics in a new field, phase contrast diffuse optical tomography (PC DOT) in which diffuse light is used to image the spatial variation of soft tissue reconstructed refractive index, and the spatial map of the reconstructed refractive index of the tissue is reconstructed by an algorithm and the results are presented as a two-dimensional, computer generated image of a cross-section of the tissue.

BACKGROUND OF THE INVENTION

Cancer in its various forms is a leading cause of death worldwide. Detection and treatment of cancer have become a highly significant burden on health care resources. As a result, research into the early detection, treatment, cure, and prevention of cancer remain high priorities in both the public and private sectors of the health care system.

Because breast cancer is a common form of cancer affecting women worldwide and remains a leading cause of death among women. In the ongoing race to present or cure breast cancer, early detection currently provides the foundation for the widest variety of successful treatment as measured by post-treatment survival rates.

The basic steps of early detection of breast cancer are well established and educational programs have improved individual practice and effectiveness. For breast cancer, early detection starts with regular, systematic self-examination to detect lumps or other abnormalities. Regular examinations by a qualified physician to detect lumps and abnormalities are the next step. Both examinations are useful and should not be abandoned, but they are limited by the experience and skill of the individual and generally family to detect small tumors or masses that generally are most responsive to treatment.

Mammography represents a significant step in identifying the presence of tumors; however, this x-ray technology is far from fail-safe in detection of tumors for a variety of reasons, including differences in patients, skill levels of technicians, and differences in interpretation of the mammogram. The low specificity of x-ray mammography suggests that many women without cancer will receive recommendations to undergo a breast biopsy. This results in up to 4-5 benign biopsy results for everyone one cancer that is detected. In addition the minimum frequency for mammography has not been clearly established, and unfortunately, the technology is not always readily available to women. Also, seemingly too many women do not avail themselves of mammography examinations, due in part to concerns about exposure to radiation and to physical discomfort. This may be largely an educational issue.

A variety of evolving technologies has been applied to the early detection of breast cancer. Technologies include the use of ultrasound to compliment mammography. CT scan technology has not been demonstrated to be markedly useful in early detection of malignant tumors. Similarly, MRI technology has not proved to be uniquely useful in early detection.

Biopsy is effective, but in addition to expenses, it is an invasive procedure with all of the inherent risks of any comparable surgical procedure. Most frequently, surgical techniques are used to follow-up questionable or medically suspicious findings based on other techniques.

Therefore, there remains room for improvement in early detection of breast cancer and other tumors, in which the detection is non-invasive and accurately identifies and locates small tumors or other abnormal growths that may not otherwise be detected using current technology.

SUMMARY OF THE INVENTION

A purpose of the invention is a system measuring the scattering and absorption of light (photon flux) in the near infrared spectral range to generate expected values using a complex algorithm to produce reconstructed spatial maps that reflect spatial variation in refractive index of soft tissue. A further purpose is a non-invasive method and system to distinguish tumors from normal tissue in soft tissue organs and to distinguish malignant from benign tumors. An additional purpose of the invention is an algorithm that utilizes observed photon flux data to generate expected values to yield reconstructed refractive index spatial maps. These and other purposes, objectives, and goals are satisfied by a method that utilizes near infrared radiation delivered to soft tissue by at least two sets of fiber optic materials positioned on the soft tissue with at least two additional, independent sets of fiber optic material positioned on the soft tissue and in communication with a computer that receives photon flux information resulting from scattering of the delivered radiation and, by means of an algorithm generates, through iterations to minimize differences between observed photon flux data and calculated values, a reconstructed spatial map, based on a pre-established grid or matrix, that reflects spatial variation in refractive index the image of which can be presented on a screen or in hard copy. The purposes, goals, and objectives of the invention are further satisfied by a method of employing an algorithm to generate reconstructed refractive index spatial maps, then determining observed (experimental) photon density values and finally by iteratively estimating obtaining expected parametric values that minimize differences with the observed values with the method employing near infrared light and fitting a pre-established mesh or grid from which spatial maps are derived. Moreover, the goals, purposes, and objectives will be further satisfied by a system in which a computer programmed with an algorithm generates expected photon density values to satisfy a photon diffusion equation and iteratively compare the generated (calculated) values with values derived from observed scattering of near infrared light delivered to the tissue by two or more bundles of fiber optical material positioned on the soft tissue and functionally connected to the light source with a second set of two or more optical fiber bundles positioned on the soft tissue and functionally connected to the computer that receives and analyzes the observed data to generate spatial variation maps that reflect differences in refractive index and the images produced permit detection of tumors and separation of certain types of malignant tumors from benign growths and from normal tissues. Finally, the goals, purposes, and objectives will be further satisfied by the images of a reconstructed refractive index spatial map produced by analyzing photon flux data from near-infrared light using an algorithm programmed into a computer capable of producing displays of the spatial maps for clinical analysis. These and other benefits, advantages, purposes, and goals will be readily apparent in the following descriptions, examples, figures, and appended claims.

BRIEF DESCRIPTION OF THE FIGURES

FIGS. 2 A-E illustrate variation in spatial maps produced by reconstruction methods from measurements made in vitro on a tissue mimicking phantom in which one or more targets (simulated tumors) had a light scattering medium different than the background medium.

DETAILED DESCRIPTIONS OF PREFERRED EMBODIEMENTS

The System

In summary, the system comprises two sets of optical fibers with each set comprising at least two bundles of fibers. The members of one set are functionally connected to a source of near infrared light. Each bundle of fibers delivers the light at predetermined locations on the tissue to be examined. The second set of bundles is in contact with the tissue in predetermined locations, detects scattered light from the light delivered to the tissue. The members of the second set of bundles are in functional communication with a computer that analyzes the scattering data as part of the total light delivered and by means of a photon diffusion equation and complex algorithm in conjunction with a pre-established two-dimensional grid or matrix, generates a reconstructed spatial map of the tissue based on the detected scattering (observed data) and expected values for all points in the grid in an iterative process such that ultimately differences between observed and expected values are minimized and a map image is produced for examination. Tumors are indicated by differences in shading or color differences, depending on the specific mode of display, and differences of the mode of display are assumed within the scope and intent of the invention.

The refractive index of most biological tissue is not a constant, even at the cellular level. Refractive index, including the closely related phenomenon of photon flux, depends on physical and chemical properties of the tissue. Refractive index and scattering are complexly correlated involving absorption parameters as well as scattering parameters. The scattering coefficient is a consequence of local refractive index distribution. Phase contrast diffuse optical tomography provides a reliable system to image soft tissue of weakly absorbing materials.

Optical image reconstruction, or model based optical imaging utilizes a photon diffusion equation to model light propagation in tissue and provide a tractable basis for image reconstruction with multiply scattered light. Modeling requires an effective reconstruction algorithm. Reconstruction methods using diffuse light are markedly superior (two- to three-fold) in resolution compared with direct imaging methods. The system and method of the present optical image reconstruction utilizes both observed absorption and scattering images with continuous-wave, near infrared tomographic measurements. An iterative algorithm that reconstructs refractive index based photon density imaging has detected tumors as small as 5 mm in human breast tissue and has distinguished between benign and malignant tumors.

Clinical Aspects

Tissue (patient's clinical) examination to collect data for optical map reconstruction utilized a near-infrared, automated, multi-channel frequency domain imager. Clinical studies employed intensity modulated light from a 785-nm 50 mW diode laser (Thorlabs, Newton, N.J., U.S.A.) transmitted sequentially via an automated, moving stage (17 NST 101, Melles-Griot, Cambridge, England) to 16 3-mm fiber optic light source bundles (source bundles) attached to the breast at designated positions. For each source position, the diffused light was detected by 16 3-mm fiber optic light source bundles (detector bundles) positioned on a plane on the surface of the breast with data sequentially to a photomultiplyer tube (R928, Hamamatsu, Middlesex, N.J., U.S.A.) via a second automated moving stage. Modulation and heterodyne frequencies were 100 MHz and 1 kHz, respectively with dynamic range and detection sensitivity of about $10^9$ and $10^{-12}$ W, respectively. It should be noted that the number of source and detector bundles is not limiting so long as it is at least two, and the invention anticipates combinations different than 16 bundles of each of the source and detector optical fiber bundles.

Figure 1:
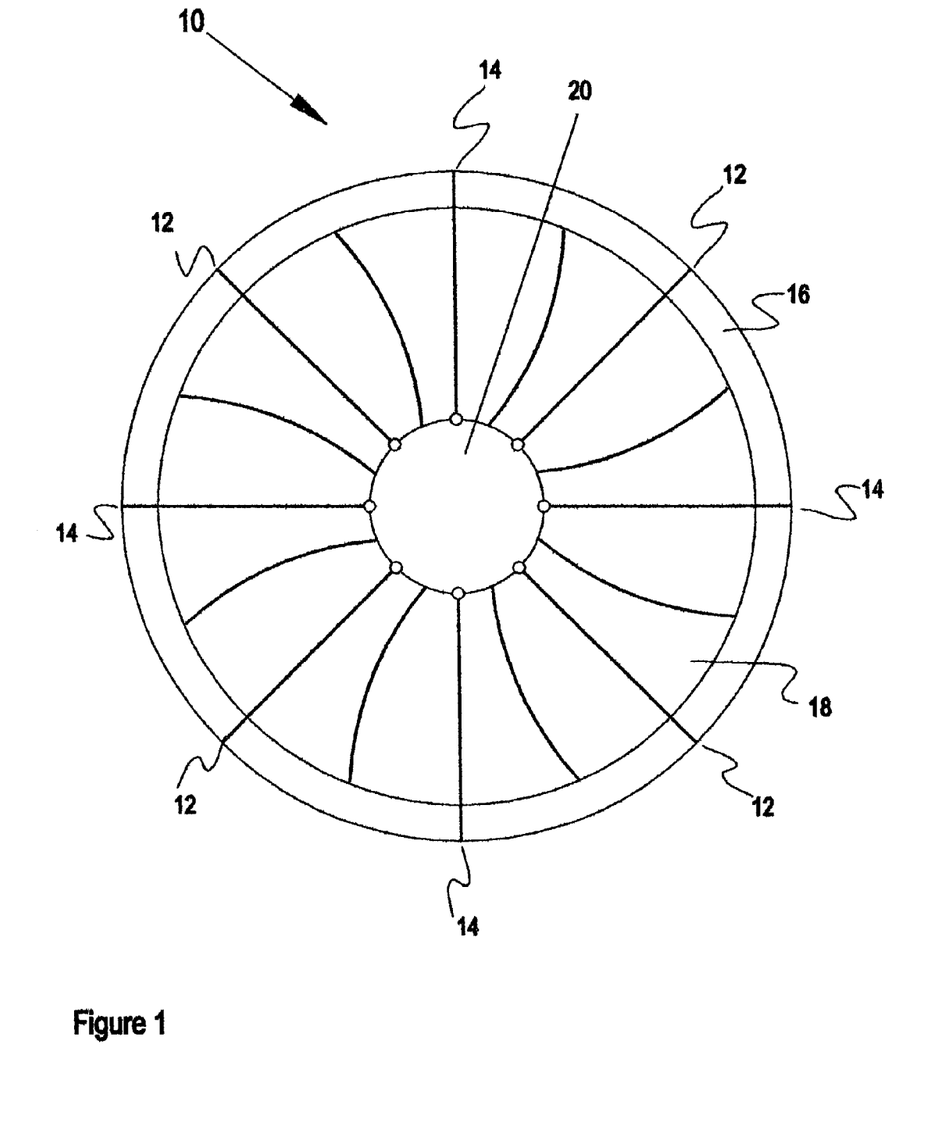
FIG. 1 is a simplified diagram of a device adapted to position fiber optic bundles on soft tissue.

As illustrated in FIG. 1, both the source optical fiber bundles 12 and the detector optical fiber bundles 14 are securely held by a plate device 10. As illustrated, a total of eight (8) optical fiber bundles, four (4) source 12 and four (4) detector 14 are shown for simplicity. In practice, but not by way of limitation, sixteen (16) of each are arranged in an alternating pattern. The source optical fibers 12 are operationally connected to a source of near-infrared light (not illustrated) and in contact with the surface of the breast, and the detector optical fibers are in functional communication with a computer capable of receiving and analyzing the photon flux information represented by the observed scattering data, of generating a spatial map based on reconstructed refractive index from a pre-established grid or matrix. Without affecting the scope or purpose of the invention, the images may be represented in shades of a single color or as colored images, and the computer is capable producing hard copies of the images.

The plate device 10 is inserted over the breast to be examined, or effectively the breast is positioned through the open center or annulus 20 of the plate device 10 thus establishing the plane on which the image will be made. The plate device 10 has a solid, rotatable outer ring that can extend or retract the vein-like elements 18 of the inner portion of the device 10 to increase or decrease the size of the open center 20 to accommodate different positions on the breast or patients with breasts of different sizes. In practice, the device 10 may be integrated into an examination table on which a patient lies face down with the breast extended through the open center 20 of the device. A two-dimensional, cross-section optical image is generated (spatial map) at a plane established by positioning the device on the breast.

In the following examples, a two-dimension, finite-element mesh with 717 nodes and 1368 triangles was established to as a basis for estimating optical values from the observed scattering data and iteratively reconstructing a refractive index based spatial map. The dimensions of the finite element mesh or grid are exemplary, and the invention anticipates other sizes as well as the use of different numbers of source and detector optical fiber bundles.

Spatial Map Recovery

Imaging on which tumor location and type are determined is based on an image reconstruction system and method including an algorithm that extracts the spatial variation of tissue refractive index using near-infrared (NIR) diffusing light. The modeling light propagation is a diffusion approximation to the radiative transfer equation for highly scattered media with spatially varying refractive index. The spatial map of refractive index is recovered (reconstructed) using a finite element base Newton-type reconstruction algorithm. Diffusion and absorption coefficients are assumed to remain constant during reconstruction of refractive index with phase-contrast imaging. The goal is to iteratively update the refractive index, n, distribution so that a weighted sum of squares difference between computed and measured optical data is minimized. In the examples presented, stable images were achieved with twenty (20) iterations.

Equation 1 describes a photon diffusion relationship considering spatially varying refractive index that forms the theoretical foundation for NIR phase contrast imaging:

$$-\frac{n}{c}\frac{\partial \Phi(r,t)}{\partial t} + \nabla \cdot D\nabla \Phi(r,t) + \frac{2D}{n}\nabla n \cdot \nabla \Phi(r,t) - \mu_a \Phi(r,t) = \\ -S_0(t)\delta(r-r_0)$$

Eq. 1

Where $\Phi$=the photon density; n=the refractive index; c=the speed of light in the medium; D=the diffusion; $\mu_a$=the absorption coefficient; $S_0$=the source strength; $\delta(r-r_0)$=Dirac delta function at position $r_0$.

When only continuous-wave or dc data are considered, $$-\frac{n}{c}\frac{\partial \Phi(r,t)}{\partial t}$$

from Eq. 1 becomes zero (0) and Eq. 1 becomes $$\nabla \cdot D\nabla \Phi(r) + \frac{2D}{n}\nabla n \cdot \nabla \Phi(r) - \mu_a \Phi(r) = -S_0\delta(r-r_0)$$

Eq. 2

With Type III boundary conditions for Eq. 2 defined by $$-D\nabla \Phi \cdot \hat{i}_n = \alpha \Phi$$

Eq. 3

Where $\hat{i}_n$=the unit normal vector for the boundary surface and $\alpha$=a coefficient related to the internal reflection at the boundary.

Finite element descretization yields a discrete matrix for Eq. 2 and other derived matrix relationships through differentiation, yielding a set of equations capable of inverse problem solution $$[A]\{\Phi\}=\{b\}$$

Eq. 4

$$[A]\left\{\frac{\partial \Phi}{\partial n}\right\} = \left\{\frac{\partial b}{\partial n}\right\} - \left[\frac{\partial A}{\partial n}\right]\{\Phi\}$$

Eq. 5

$$(\mathfrak{F}^T\mathfrak{F}+\lambda I)\Delta n = \mathfrak{F}^T(\Phi^{(m)}-\Phi^{(c)})$$

Eq. 6

Where the elements of the matrix [A] are $a_{ij}=\langle -D\nabla\phi_j \cdot \Delta\phi_i - \mu_a\phi_j\phi_i\rangle$, where $\langle \ \rangle$ indicates integration over the probable domain; $\phi_i$ and $\phi_j$ are locally spatially varying Lagrangian basic functions at nodes i and j, respectively; $\mathfrak{F}$ is the Jacobian matrix that should be formed by $\partial \Phi/\partial n$ on at the boundary measurement sites; $\Delta n=(\Delta n_1, \Delta n_2, \Delta n_N)^T$ is the updated vector for the refractive index profile where N is the total number of nodes in the finite element mesh used; $\Phi^{(m)}=(\Phi_1^{(m)}, \Phi_2^{(m)}, \ldots \Phi_M^{(m)})$ and $\Phi^{(c)}=(\Phi_1^{(c)}, \Phi_2^{(c)}, \ldots \Phi_M^{(c)})$ where $\Phi_i^{(m)}$ and $\Phi_i^{(c)}$, respectively, are measured (m) and calculated (c) data for i=1,2, ... M boundary locations.

The reconstruction algorithm is verified by the use of tissue-like, phantom (in vitro) measurements with known targets and by in vivo studies the results of which have been confirmed by biopsy. In the following, Example 1 illustrates the phantom studies with known targets and Example 2 illustrates clinical (in vivo) studies subsequently verified by biopsy.

EXAMPLE 1

Phantom measurements in vitro using tissue-like materials with different contrasts of reconstructed refractive index between targets (simulated tumors or abnormal tissue) and background material illustrate the application of the reconstruction algorithm and total system in identifying abnormal tissue. A background lipid emulsion solution (Intralipid) was used to mimic tissue scattering (reduced scattering coefficient ($\mu_s'$)=1.0 mm$^{-1}$). India ink (absorption coefficient=0.007 mm$^{-1}$) was used to simulate tissue absorption. Agar powder (2%) was used to solidify the Intralipid/India ink solution yielding a background material with a refractive index close to that of water (n=1.33 and $\lambda$=785 nm, where n is the refractive index and $\lambda$ the wave length of the light used). Targets in the background material represented one of two cases: essentially void holes (air, n=1.0) or mixtures of sugar (glucose, 60%) and Intralipid/India ink solution (n=1.47).

Five phantom situations were evaluated, three produced reconstructed, refractive index spatial maps for highly scattering targets and two for low scattering targets (i.e. air). The images created in response to highly scattering target material (n=1.47) appear as markedly darker areas on the spatial map display (FIGS. 2A-C. Whereas, the images the images created in response to the low scattering material (n=1.0) appear as well defined bright areas on the spatial map displays (FIGS. 2D and E). The apparent reversal of images is due in part to the fact that the reconstructed refractive indexes involve both scattering and absorption, and the different targets differ markedly in these two properties. Detection of this difference also explains in part why malignant tumors can be distinguished from benign tumors. For FIGS. 2A-E, $\mu_a$=the absorption coefficient of the target, $\mu_s'$=the reduced scattering coefficient of the background, and n=the refractive index. For each figure, the background material was a lipid emulsion solution with n=1.33, relatively close to the refractive index of water.

Figure 2A:
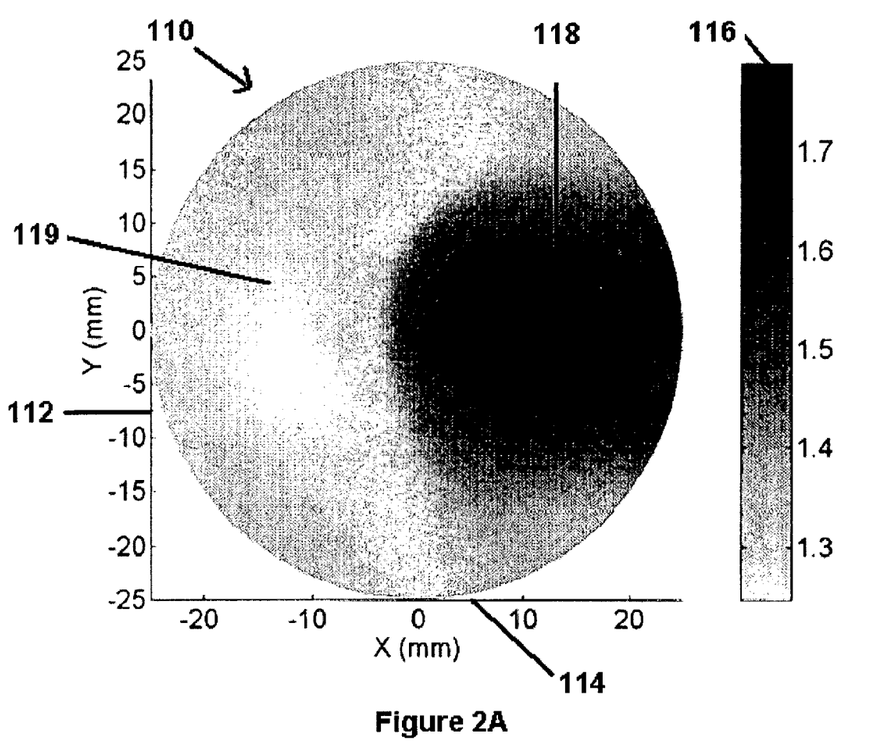

FIG. 2A illustrates the map image 116 of a reconstructed refractive index spatial map from measurements of scattering of near-infrared light in which a single target 119 was filled with a highly scattering mixture comprising glucose (1%), Intralipid, and India ink: n=1.47, $\mu_a$=0.007 mm$^{-1}$, and $\mu_s'$=1.0 mm$^{-1}$. The vertical axis 112 and horizontal axis 114 provide a size scale (mm). The color density scale 116 provides a comparison basis of the relative magnitude of the reconstructed refractive index spatial variation. The single target 118 is clearly from the background 119 as a much darker area with somewhat indefinite margins.

Figure 2B:
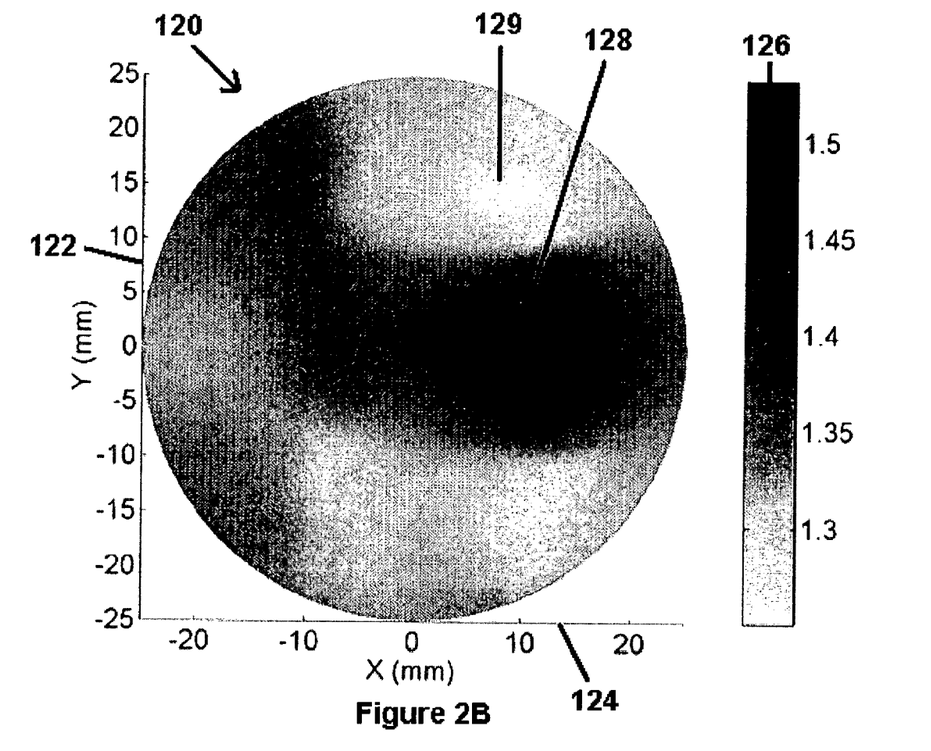

FIG. 2B illustrates the map image 120 of a reconstructed refractive index spatial map made from measurements of scattering near-infrared light in which a single target 129 was filled with a highly scattering mixture comprising glucose (3%), Interlipid, and India ink: n=1.47, $\mu_a$=0.028 mm$^{-1}$, $\mu_s'$=3.0 mm$^{-1}$. The vertical axis 122 and horizontal axis 124 provide a size scale (mm). The color density scale 126 provides a comparison basis of the relative magnitude of the relative magnitude reconstructed refractive index spatial variation. The single target 128 is clearly distinguishable as a darker area from the lighter background material 129. Like FIG. 1A, the margins of the target are somewhat indefinite.

Figure 2C:
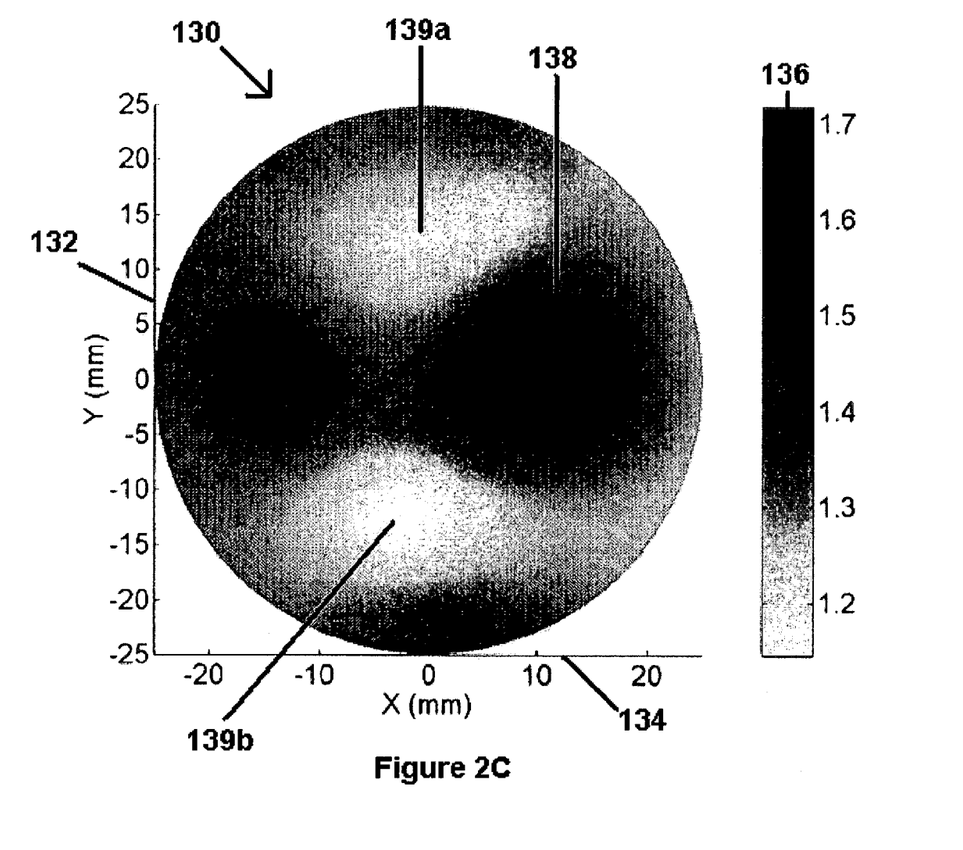
Figure 2D:
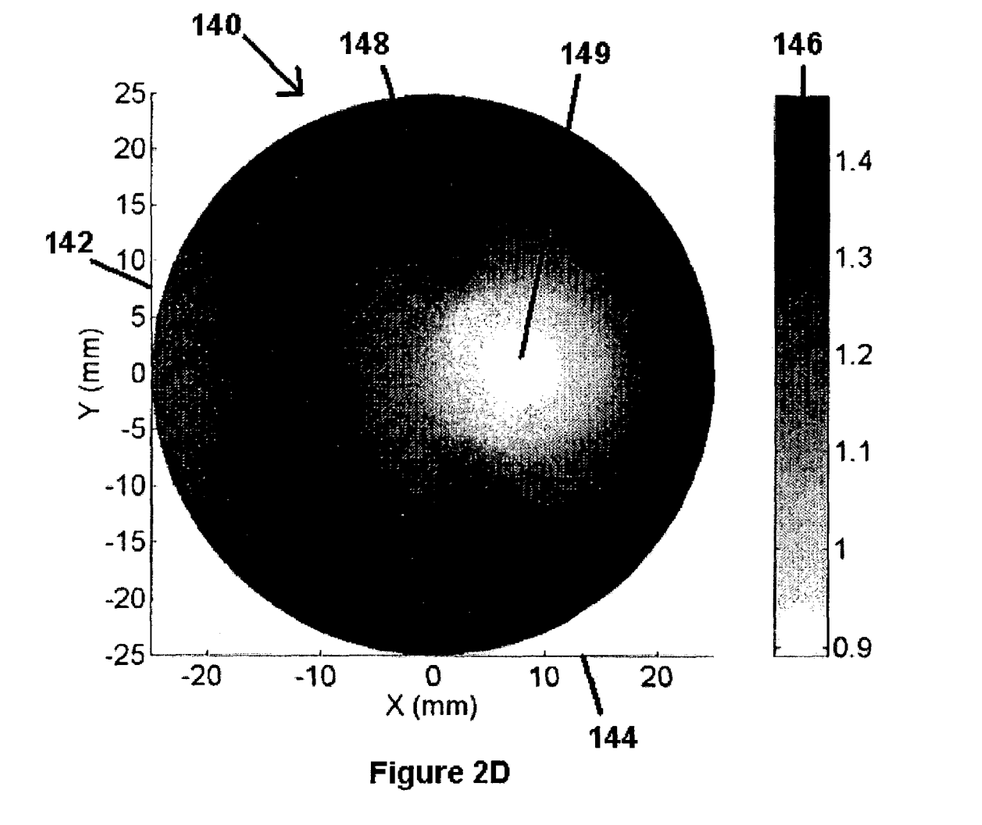

FIG. 2C illustrates the map image 130 of a reconstructed refractive index spatial map made from measurements of scattering near-infrared light in which two targets 139a and 139b were filled with a highly scattering mixture comprising glucose (1%), Interlipid, and India ink: n=1.47, $\mu_a$=0.007 mm$^{-1}$, and $\mu_s'$=1.0 mm$^{-1}$. The vertical axis 132 and horizontal axis 134 provide a size scale (mm). The color density scale 136 provides a comparison basis of the relative magnitude of reconstructed refractive index spatial variation. The background 139 is clearly distinguishable from the targets 138A and 138B, which are mutually distinguishable.

FIG. 2D illustrates the map image 140 of a reconstructed refractive index spatial map made from measurements of scattering near-infrared light in which a single target 149 was filled with a low scattering mixture (air) in which n=1.0, $\mu_a$=0 mm$^{-1}$, and $\mu_s'$=0 mm$^{-1}$. The vertical axis 142 and the horizontal axis 144 provide a size scale (mm). The color density scale 146 provides a comparison basis of the relative magnitude or reconstructed refractive spatial variation. The background 148 is clearly distinguishable from the target that appears as a bright area 149.

Figure 2E:
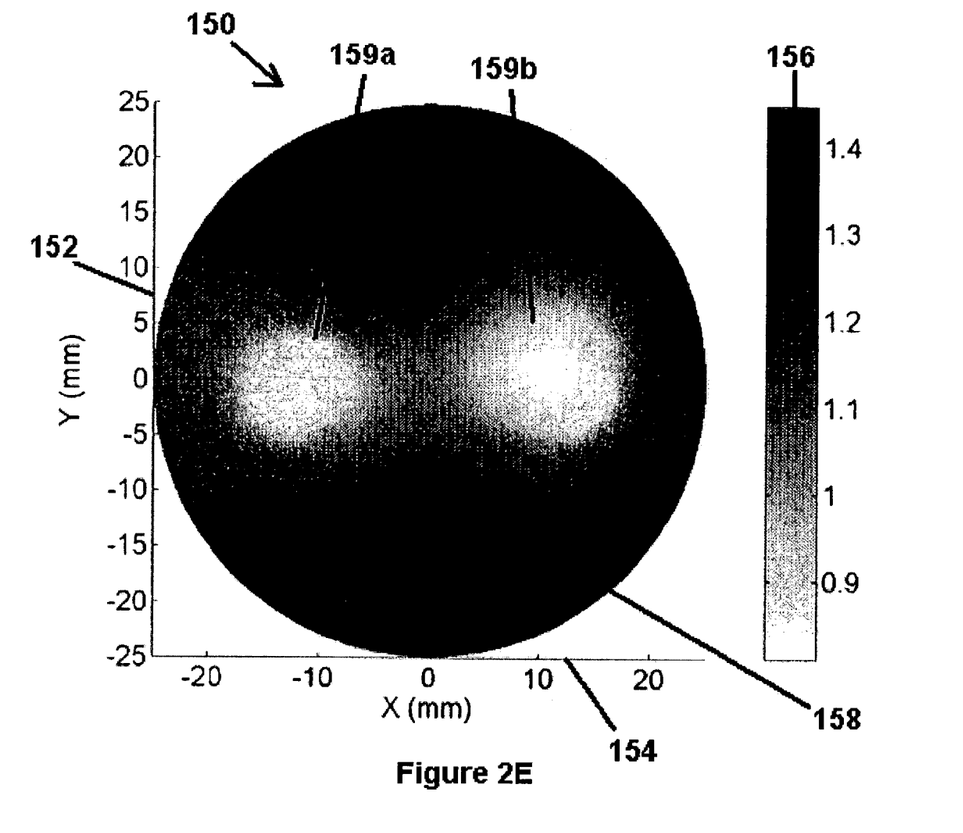

FIG. 2E illustrates the map image 150 of a reconstructed refractive index spatial map made from measurements of scattering near-infrared light in which two targets 159A and 159B were filled with a low scattering mixture (air) in which n=1.0, $\mu_a$=0 mm$^{-1}$, and $\mu_s'$=0 mm$^{-1}$. The vertical axis 152 and horizontal axis 154 provide a size scale (mm). The color density scale 156 provides a comparison basis of the relative magnitude of reconstructive refractive index spatial variation. The two targets 159A and 159B are clearly distinguishable from the background 158 and are mutually distinguishable.

Considering all five illustrations of this example, clearly the targets are distinguishable from the background. Differences in size and the relative color density that indicates spatial variation in refractive index based on the reconstruction of that index to generate a reconstructed refractive index effectively distinguish targets based on low-scattering and high-scattering materials. Differences are further reflected in parallel clinical studies with human subjects.

EXAMPLE 2

Figure 3A:
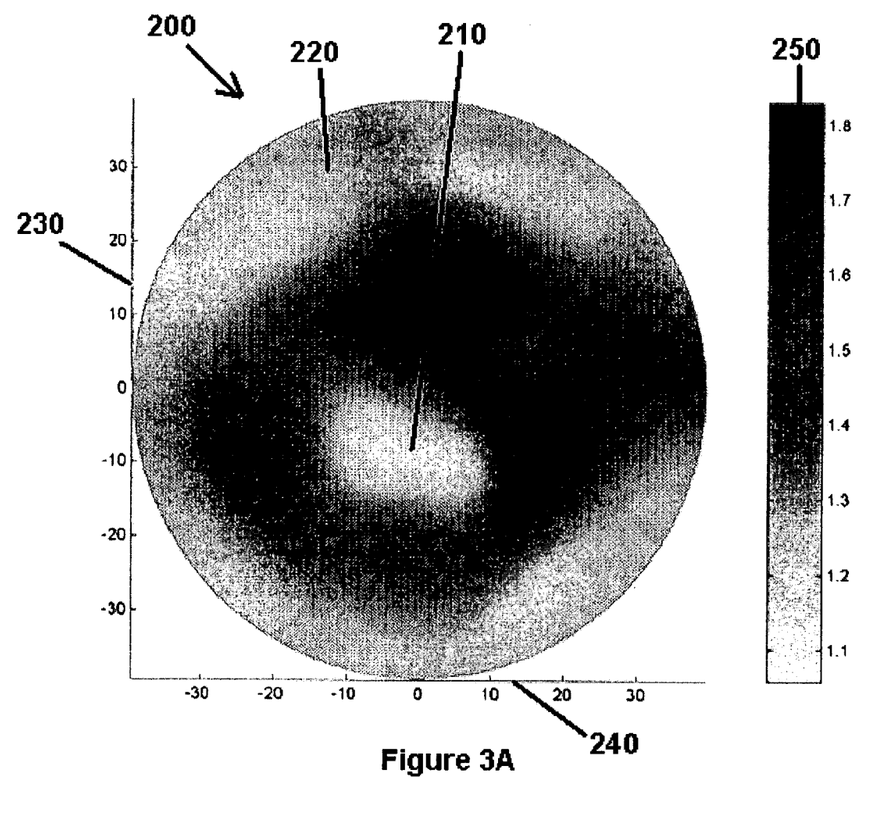
FIG. 3A and B illustrate abnormalities using photon density observations to generate reconstructed spatial variation maps that represent variations in refractive index in the tissue illustrated.
Figure 3B:
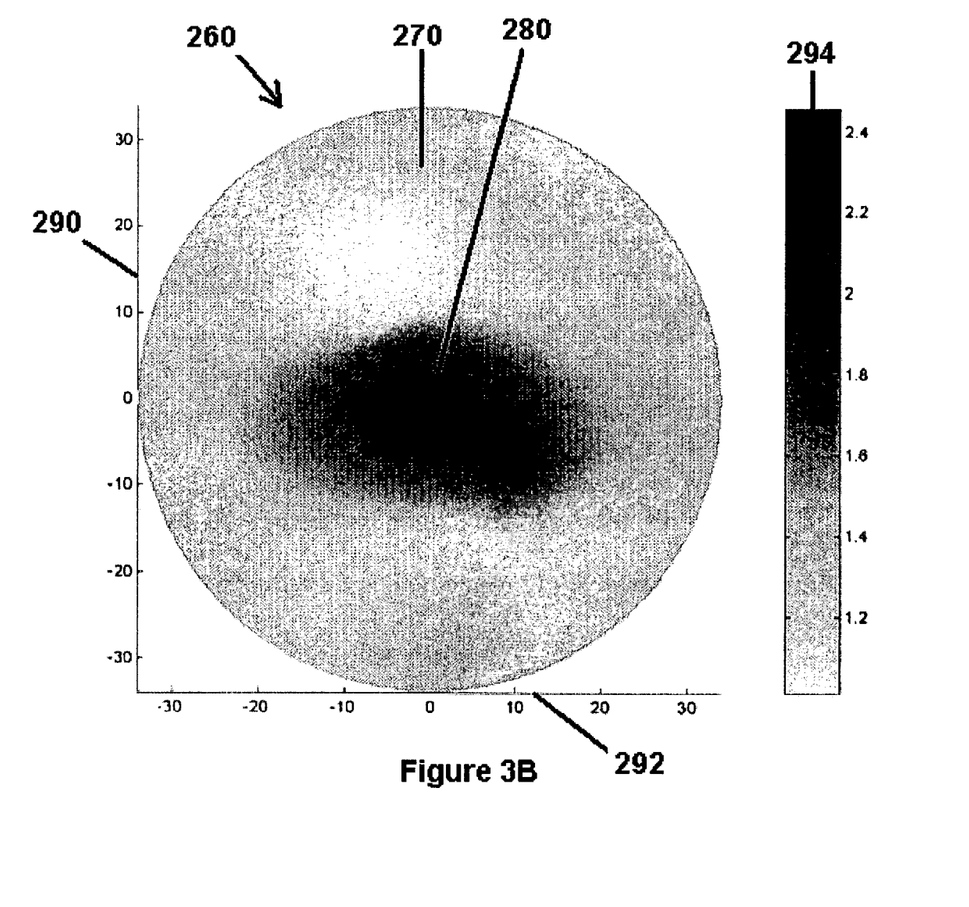

The ultimate utility of the invention is realized in the production of reconstructed refractive index spatial maps, the images of which allow the identification of tumorous tissue and distinguishes between benign and malignant tumors. FIGS. 3A and 3B illustrate clinical applications of the system and methods of this invention following the same theories of Example 1.

FIG. 3A illustrates the image of a reconstructed refractive index spatial map utilizing near infrared light in the examination of breast tissue of a 39 year-old, female patient. The image 200 reveals a relatively light, well defined area 210 below and to the left of the center of the field, compared with the background material 220. This suggests a tumorous mass at the indicated position at least in part within the plane of the spatial map of reconstructed refractive index. Low refractive index is characteristic of certain types of malignant tumors. The image of the spatial map and conclusion that a malignant tumor was present justified a subsequent biopsy that confirmed the presence of an approximately 2 cm, infiltrating ductal carcinoma (malignant tumor). Smaller tumors can be detected. Similar to other illustrations, the vertical axis 230 and horizontal axis 240 provide a size scale (mm). The color density scale 250 provides a comparison basis of the relative magnitude reconstructed refractive index spatial variation.

FIG. 3B illustrates the image of a reconstructed refractive index spatial map utilizing near-infrared light in the examination of the breast tissue of a 69 year old female patient. The image 260 reveals a relatively dark, well defined area 280 near the bottom center of the field, compared with the background material 270. This suggests some type of mass at the indicated position at least in part within the plane of the spatial map. The dark area indicates an area of relatively high refractive index, a condition not common to malignant tumors. A biopsy subsequent to the examination revealed the presence of a 2 cm cyst.

Comparing FIGS. 3A and 3B reveals that reconstructed refractive index spatial maps may display two distinct types of images, and these may distinguish malignant from benign tissues.

What I claim is:

1. A method to produce a reconstructed refractive index spatial map useful for detection of a tumor in tissue comprising the following steps:
   a. utilizing light in the near-infrared portion of the spectrum as a source of illumination;
   b. generating observed values representing photon flux by delivering said light in the near-infrared portion of the spectrum to a surface of the tissue to be examined by at least two bundles of source optical fibers;
   c. detecting scattered photons from said light in the near-infrared portion of the spectrum by at least two bundles of detector optical fibers, said at least two bundles of detector optical fibers being in functional communication with a computer;
   d. processing the detected scattered photon data received by said computer to generate expected parametric values related to refractive index by means of an algorithm programmed into said computer, wherein said algorithm is based on the solution of:

$$-\frac{n}{c}\frac{\partial \Phi(r,t)}{\partial t} + \nabla \cdot D\nabla\Phi(r,t) + \frac{2D}{n}\nabla n \cdot \nabla\Phi(r,t) - \mu_a\Phi(r,t) =$$
$$-S_0(t)\delta(r-r_0)$$

where $\Phi$=the photon density; n=the refractive index; c=the speed of light in the medium; D=the diffusion; $\mu_a$=the absorption coefficient; $S_0$=the source strength; $\delta(r-r_0)$ Dirac delta function at position $r_0$;

e. iteratively comparing said observed and said calculated values related to refractive index until differences between values are non-significant;

f. producing an image of the reconstructed refractive image spatial map; and g. evaluating the said spatial map to determine if abnormalities are apparent in the mapped tissue.

2. The method of claim 1 wherein said tissue is human breast tissue.

3. A method to detect a tumor in tissue comprising the steps of:

a. assigning initial values to elements of a photon diffusion equation;

b. determining photon density values experimentally;

c. calculating refractive index values reiteratively using an algorithm based on the solution of:

$$-\frac{n}{c}\frac{\partial \Phi(r,t)}{\partial t} + \nabla \cdot D\nabla \Phi(r,t) + \frac{2D}{n}\nabla n \cdot \nabla \Phi(r,t) - \mu_a \Phi(r,t) = -S_0(t)\delta(r-r_0)$$

Where $\Phi$=the photon density; n=the refractive index; c=the speed of light in the medium; D=the diffusion; $\mu_a$=the absorption coefficient; $S_0$=the source strength; $\delta(r-r_0)$ =Dirac delta function at position $r_0$ and d. generating a refractive index spatial map for detection of a tumor using the calculated refractive index values.

4. A system to produce reconstructed refractive index spatial maps comprising:

a. at least two bundles of detector fiber optic material in functional communication with a computer, said computer adapted to receive observed photon density data ands to analyze said data by means of an algorithm;

b. at least two bundles of fiber optic delivery material functionally connected to a light source, said light source being adapted to transmitting light in the near-infrared portion of the spectrum;

c. an algorithm based on the solution of:

$$-\frac{n}{c}\frac{\partial \Phi(r,t)}{\partial t} + \nabla \cdot D\nabla \Phi(r,t) + \frac{2D}{n}\nabla n \cdot \nabla \Phi(r,t) - \mu_a \Phi(r,t) = -S_0(t)\delta(r-r_0)$$

where $\Phi$=the photon density; n=the refractive index; c=the speed of light in the medium; D=the diffusion; $\mu_a$=the absorption coefficient; $S_0$=the source strength; $\delta(r-r_0)$ =Dirac delta function at position $r_0$;

said algorithm capable of the analysis of photon density observed data communicated to it to generate a restructured refractive index map of tissue being examined, said spatial map being produced by iterations of points on a predetermined grid; and d. A means to display and reproduce said spatial map.

5. The reconstructed refractive index spatial maps displayed in any form, said map being produced by the analysis of photon scattering using light in the near-infrared portion of the spectrum wherein photon scattering data are transmitted to a computer capable of analysis of said data by means of an algorithm based on the solution of:

$$-\frac{n}{c}\frac{\partial \Phi(r,t)}{\partial t} + \nabla \cdot D\nabla \Phi(r,t) + \frac{2D}{n}\nabla n \cdot \nabla \Phi(r,t) - \mu_a \Phi(r,t) = -S_0(t)\delta(r-r_0)$$

where $\Phi$=the photon density; n=the refractive index; c=the speed of light in the medium; D=the diffusion; $\mu_a$=the absorption coefficient; $S_0$=the source strength; $\delta(r-r_0)$ =Dirac delta function at position $r_0$, ultimately yielding a reconstructed refractive index spatial map.

* * * * *